United States Patent [19]

Breitzke et al.

[11] Patent Number: 4,876,035

[45] Date of Patent: Oct. 24, 1989

[54] AQUEOUS PREPARATIONS OF SODIUM LAURYL SULFATE AND MYRISTYL SULFATE HAVING A LOW CLOUD POINT USEFUL IN MAKING TOOTHPASTES

[75] Inventors: Willi Breitzke, Duesseldorf; Hermann Hensen, Hilden, both of Fed. Rep. of Germany

[73] Assignee: Henkel Kommanditgesellschaft auf Aktien, Duesseldorf, Fed. Rep. of Germany

[21] Appl. No.: 57,468

[22] Filed: Jun. 3, 1987

[30] Foreign Application Priority Data

Jun. 9, 1986 [DE] Fed. Rep. of Germany ....... 3619358

[51] Int. Cl.$^4$ .......................... A61K 7/16; C11D 1/14; C11D 1/83; C11D 3/43
[52] U.S. Cl. ................................ 252/550; 252/170; 252/171; 252/173; 252/174.21; 252/174.22; 252/353; 252/DIG. 1; 252/DIG. 14; 424/49; 424/56
[58] Field of Search ............. 252/550, 174.23, DIG. 1, 252/DIG. 2, DIG. 14, 170, 171, 173, 174.21, 353; 424/49, 56

[56] References Cited

U.S. PATENT DOCUMENTS

| | | | |
|---|---|---|---|
| 4,041,149 | 8/1977 | Gaffar | 424/57 |
| 4,130,636 | 12/1978 | Tomlinson | 424/52 |
| 4,132,770 | 1/1979 | Barth | 424/49 |
| 4,465,661 | 8/1984 | Schmolka | 424/49 |
| 4,469,674 | 9/1984 | Shah | 424/52 |

FOREIGN PATENT DOCUMENTS

| | | |
|---|---|---|
| 0002594 | 6/1979 | European Pat. Off. |
| 0145065 | 6/1985 | European Pat. Off. |
| 836774 | 6/1960 | United Kingdom |

OTHER PUBLICATIONS

Patent Abstract of Japan, vol. 5, No. 144 (C-71)(816), J. Am. Oil Chem. Soc. 48, (Nov. 71), 674–677.
Fette, Seifen, Anstrichmittel.

*Primary Examiner*—Dennis Albrecht
*Assistant Examiner*—Kathlene Markowski
*Attorney, Agent, or Firm*—Ernie G. Szoke; Wayne C. Jaeschke; Real J. Gradmaison

[57] ABSTRACT

Clear, aqueous liquid preparations of sodium lauryl sulfate and myristyl sulfate comprising from 5 to 20% by weight of sodium lauryl sulfate and/or myristyl sulfate, from 10 to 30% by weight of a nonionic surface-active ethylene oxide adduct having an HLB-value of from 12 to 18, from 10 to 20% by weight of a polyol containing from 3 to 6 carbon atoms and from 2 to 6 hydroxyl gropus or a polyethylene glycol, and from 30 to 75% by weight of water, are distinguished by low cloud points and are suitable for use as a surfactant component in the production of oral hygiene products such as toothpastes.

18 Claims, No Drawings

AQUEOUS PREPARATIONS OF SODIUM LAURYL SULFATE AND MYRISTYL SULFATE HAVING A LOW CLOUD POINT USEFUL IN MAKING TOOTHPASTES

BACKGROUND OF THE INVENTION

1. Field of the Invention

This invention relates to clear, aqueous liquid preparations of sodium salts of linear alkylsulfates which, by virtue of their composition and performance properties, are particularly suitable for use as surfactant components in the manufacture of toothpastes.

2. Discussion of Related Art

Dilute aqueous solutions of sodium-n-alkylsulfates containing from 12 to 16 carbon atoms show a tendency towards clouding and precipitation of undissolved alkylsulfate, even at temperatures above 10° C. The reason for this is the relatively poor solubility of these alkylsulfates in water at temperatures below the critical solution temperature or rather the Krafft temperature, i.e., the temperature above which there is a sudden increase in water solubility through increased micelle formation. In the case of sodium dodecylsulfate, for example, this temperature is at 8° C. and, for sodium tetradecylsulfate, is at 20.5° C. (cf. H. Lange and M. J. Schwuger, KolloidZeitschrift and Zeitschrift fur Polymere, Vol. 223 (1967), pages 145 to 149).

Sodium-n-alkylsulfates are suitable for numerous commercial applications by virtue of their favorable foaming properties and their cleaning effect. Their neutral flavor, their acceptable compatibility with mucous membrane, and their growth-inhibition effect on the bacteria responsible for plaque make them particularly suitable for use as a surfactant component in the production of oral hygiene and dental care preparations. The products are typicaly used as spray-dried or recrystallized, fine crystalline powders for these applications. This gives rise to the disadvantage of considerable dust emission in use and the unwanted entry of air into the product.

The use of the products in dissolved form is prevented by their limited solubility in water. It has previously been proposed to mix the sodium-n-alkylsulfates with water and glycerol and/or sorbitol, however, the suspension obtained has to be subjected to prolonged degassing at elevated temperature before it can be used in the production of toothpastes.

Accordingly, there is a need for an aqueous preparation of sodium-n-alkylsulfates in the form of a clear solution having a low cloud point which is suitable for the practical application of the sodium-n-alkylsulfates, particularly for the production of toothpastes and mouth lotions, without any of the disadvantages mentioned above

DESCRIPTION OF THE INVENTION

Other than in the operating examples, or where otherwise indicated, all numbers expressing quantities of ingredients or reaction conditions used herein are to be understood as modified in all instances by the term "about".

Therefore, it is an object of the present invention to provide a clear, aqueous liquid preparation containing a sodium-n-alkylsulfate having a low cloud point, comprising: from 5 to 20% by weight of sodium lauryl sulfate and/or myristyl sulfate, from 10 to 30% by weight of a surface-active, nonionic ethylene oxide adduct having an HLB-value of from 12 to 18, from 10 to 20% by weight of a polyol containing from 3 to 6 carbon atoms and from 2 to 6 hydroxyl groups or a polyethylene glycol, and from 30 to 75% by weight of water, based on the weight of the preparation.

In addition to the required content of sodium lauryl sulfate and/or myristyl sulfate, a small quantity of sodium-n-alkylsulfate containing 8, 10, 16 or 18 carbon atoms, of the type present as a secondary product in commercial sodium lauryl sulfate based on coconut oil fatty alcohol cuts, are not a disadvantage.

Suitable surface-active, nonionic ethylene oxide adducts include the addition products of ethylene oxide with fatty acids, fatty acidpolyol partial esters, for example with mono- and diesters of glycerol, pentaerythritol and sorbitol of $C_{12}$–$C_{22}$ fatty acids, ricinoleic acid and 9-hydroxystearic acid. Ethoxylation products of castor oil and hydrogenated castor oil, i.e., the reaction products of triglycerides with ethylene oxide, are also particularly suitable. Adducts of ethylene oxide with $C_{12}$–$C_{22}$ fatty alcohols, with fatty acid amides or alkanolamides based on $C_{12}$–$C_{22}$ fatty acids, and with alkylphenols containing $C_8$–$C_{12}$ alkyl groups are also suitable.

The ratio by weight of hydrophilic to lipophilic groups in these ethylene oxide adducts should be such that the weight of the hydrophilic glycol ether groups, formed from ethylene oxide and, optionally, from polyols, makes up from 60 to 80% by weight of the total molecule of the ethylene oxide adducts. In these ethylene oxide adducts which are suitable for the production of the preparations according to the invention, the HLB-value according to the formula $HLB=(E+P)/5$ (E=ethylene oxide content in % by weight and P=polyolether content in % by weight in the adduct) is in the range of from 12 to 18.

Suitable polyols containing from 3 to 6 carbon atoms include, for example, 1,2-propylene glycol, 1,3-propylene glycol, erythritol, glycerol, pentaerythritol, neopentyl glycol and sorbitol. Preferred polyethylene glycols include liquid polyethylene glycols having an average molecular weight of from 200 to 700. Glycerol, sorbitol, and also polyethylene glycols are preferred for use in toothpastes.

Aqueous preparations according to the invention comprising:

from 8 to 12% by weight of sodium lauryl sulfate-myristyl sulfate based on a lauryl-myristyl alcohol mixture of from 30 to 70% by weight lauryl and from 30 to 70% by weight myristyl alcohol, from 20 to 25% by weight of a castor oil ethoxylate containing from 60 to 70% by weight of glycol ether groups, from 12 to 18% by weight of glycerol, sorbitol and-/or polyethylene glycol, and from 45 to 60% by weight of water have particularly low cloud points.

That is, the clear, aqueous liquid preparations containing a sodium-n-alkylsulfate according to the invention have cloud points below 6° C., so that there is no danger of clouding or sedimentation, even in the event of prolonged storage in a cold room. They are eminently suitable for use as surfactant components for the production of oral hygiene and dental care preparations, because the addition of the surfactant in the form of such preparations is not accompanied either by dust emission or by the undesirable entry of air into the toothpaste mixture. The components of the preparations according to the invention are not undesirable and, in many cases, are desired constituents of toothpastes.

The invention is illustrated by the following examples:

EXAMPLES

The clear aqueous preparations shown in the following Table were prepared as follows:

A mixture of water and polyol (or polyethylene glycol) was initially introduced at 20° C. into a container, the lauryl-myristyl sulfate was dissolved therein while stirring and, finally, the surface-active ethylene oxide adduct was mixed in with stirring.

The cold cloud point of the aqueous surfactant preparations was determined in accordance with DIN ISO 3015.

Products commercially available under the following tradenames were used:

| | |
|---|---|
| Texapon ® LS highly conc. needles | sodium lauryl-myristyl ($C_{12}:C_{14}$ = 70:30) sulfate, |
| Eumulgin ® RO 40 | castor oil ethoxylate (approx. 40 moles of ethylene oxide per mole of castor oil), |
| Eumulgin ® SML 20 | sorbitan monolaurate-ethoxylate (20 moles of ethylene oxide), |
| Eumulgin ® 286 | nonylphenol ethoxylate (approx. 9.5 moles of ethylene oxide). |

We claim:

1. A clear, aqueous liquid preparation having a cloud point below about 6° C., said preparation consisting essentially of; from about 5 to about 20% by weight of sodium lauryl sulfate and/or myristyl sulfate, from about 10 to about 30% by weight of a surface-active nonionic ethylene oxide adduct having an HLB-value of from about 12 to about 18, from about 10 to about 20% by weight of a polyol containing from about 3 to about 6 carbon atoms and from about 2 to about 6 hydroxyl groups or a polyethylene glycol, and from about 30 to about 75% by weight of water, based on the weight of the preparation.

2. A preparation as in claim 1 including a small quantity of sodium-n-alkylsulfate containing 8, 10, 16 or 18 carbon atoms.

3. A preparation as in claim 1 wherein said nonionic ethylene oxide adduct comprises the addition product of ethylene oxide with a fatty acid or a fatty acid-polyol partial ester.

4. A preparation as in claim 1 wherein said nonionc ethylene oxide adduct comprises the ethyoxylation product of castor oil or hydrogenated castor oil.

5. A preparation as in claim 1 wherein said nonionic ethylene oxide adduct comprises a $C_{12}-C_{22}$ fatty alcohol, a fatty acid amide or alkanolamide, or an alkylphenol containing $C_8-C_{12}$ alkyl groups.

6. A preparation as in claim 1 wherein the ratio by weight of hydrophilic to lipophilic groups in said ethylene oxide adduct is such that the weight of hydrophilic glycol ether groups is from about 60 to about 80% by weight of said adduct.

7. A preparation as in claim 1 wherein said polyethylene glycol has an average molecular weight of from about 200 to about 700.

8. A preparation as in claim 1 wherein said polyol is selected from glycerol and sorbitol.

9. A preparation as in claim 1 consisting essentially of; from about 8 to about 12% by weight of a sodium laurylmyristyl sulfate, from about 20 to about 25% by weight of a castor oil ethoxylate containing from 60 to 70% by weight of glycol ether groups, from about 12 to about 18% by weight glycerol, sorbitol or a polyethylene glycol, and from about 45 to about 60% by weight water, based on the weight of the preparation.

10. A process of preparing an oral hygiene composition comprising adding to said oral hygiene composition a clear, aqueous liquid preparation having a cloud point below about 6° C., and consisting essentially of; from 5 to 20% by weight of sodium lauryl sulfate and/or myristyl sulfate, from 10 to 30% by weight of a surface-active, nonionic ethylene oxide adduct having an HLB-value of from 12 to 18, from 10 to 20% by weight of a polyol containing from 3 to 6 carbon atoms and from 2 to 6 hydroxyl groups or a polyethylene glycol, and from 30 to 75% by weight of water, based on the weight of said preparation.

11. A process as in claim 10 including a small quantity of sodium-n-alkylsulfate containing 8, 10, 16 or 18 carbon atoms.

12. A process as in claim 10 wherein said nonionic ethylene oxide adduct comprises the addition product of ethylene oxide with a fatty acid or a fatty acid-polyol partial ester.

13. A process as in claim 10 wherein said nonionic ethylene oxide adduct comprises the ethoxylation product of castor oil or hydrogenated castor oil.

14. A process as in claim 10 wherein said nonionic ethylene oxide adduct comprises a $C_{12}-C_{22}$ fatty alcohol, a fatty acid amide or alkanolamide, or an alkylphenol containing $C_8-C_{12}$ alkyl groups.

15. A process as in claim 10 wherein the ratio by weight of hydrophilic to lipophilic groups in said ethylene oxide adduct is such that the weight of hydrophilic glycol ether groups is from about 60 to about 80% by weight of said adduct.

16. A process as in claim 10 wherein said polyethylene glycol has an average molecular weight of from about 200 to about 700.

TABLE

| | | | | | | | | | | | | | | | | |
|---|---|---|---|---|---|---|---|---|---|---|---|---|---|---|---|---|
| Texapon LS highly conc. needles | 10.2 | 10.2 | 9.0 | 20.0 | 20.0 | 10.2 | 17.0 | 9.0 | 10.2 | 17.0 | 10.2 | 17.0 | 10.2 | 10.2 | 10.2 | 17.0 |
| Eumulgin RO 40 | — | 25.0 | — | — | — | 25.0 | — | — | 23.3 | — | — | — | 25.0 | — | — | — |
| Emulgin SML 20 | — | — | 23.3 | — | — | — | — | — | — | — | 15.0 | 23.3 | — | 15.0 | — | 23.3 |
| Eumulgin 286 | 23.3 | — | — | 23.3 | 23.3 | — | 23.3 | 23.3 | — | 23.3 | — | — | — | — | 15.0 | — |
| Glycerol | 15.0 | 15.0 | 15.0 | 15.0 | — | — | — | — | — | — | — | — | — | — | — | — |
| Sorbitol (70% in water) | — | — | — | — | 15.0 | 15.0 | — | — | — | — | — | — | — | — | 15.0 | 15.0 |
| Propylene glycol | — | — | — | — | — | — | 15.0 | 15.0 | 15.0 | — | — | — | — | — | — | — |
| Polyethylene glycol (av. mol. weight 200) | — | — | — | — | — | — | — | — | — | 15.0 | 15.0 | 15.0 | 15.0 | 15.0 | — | — |
| Water | 51.5 | 49.8 | 52.7 | 41.7 | 41.7 | 49.8 | 44.7 | 52.7 | 51.5 | 44.7 | 59.8 | 44.7 | 49.8 | 59.8 | 59.8 | 44.7 |
| Cloud point below °C. | 0° | 0° | +6° | +6° | +6° | 0° | +6° | 0° | +6° | 0° | +6° | +6° | 0° | +6° | 0° | +6° |

17. A process as in claim 10 wherein said polyol is selected from glycerol and sorbitol.

18. A process as in claim 10 wherein said liquid preparation consists essentially of; from about 8 to about 12% by weight of sodium lauryl-myristyl sulfate, from about 20 to about 25% by weight of a castor oil ethoxylate containing from 60 to 70% by weight of glycol ether groups, from about 12 to about 18% by weight glycerol, sorbitol or polyethylene glycol, and from about 45 to about 60% by weight water, based on the weight of said preparation.

* * * * *